United States Patent [19]
Kelly et al.

[11] Patent Number: 6,146,668
[45] Date of Patent: Nov. 14, 2000

[54] PREPARATION OF ISOFLAVONES FROM LEGUMES

[75] Inventors: Graham E. Kelly, Northbridge; Jiu Li Huang, Lane Cove; Mark G. Deacon-Shaw, Koolewong; Mark A. Waring, Elanora Heights, all of Australia

[73] Assignee: Novogen, Inc., Wilmington, Del.

[21] Appl. No.: 08/847,850

[22] Filed: Apr. 28, 1997

[51] Int. Cl.[7] ............................. C21P 21/06; C12N 9/24; A61K 31/337; A61K 35/78

[52] U.S. Cl. ............................... 426/46; 426/48; 426/52; 426/634; 435/68.1; 435/76; 435/125; 435/200; 435/272

[58] Field of Search ................... 426/598, 634, 426/545, 546, 46, 48, 52; 435/68.1, 76, 125, 200, 272

[56] References Cited

U.S. PATENT DOCUMENTS

| | | | |
|---|---|---|---|
| 3,973,608 | 8/1976 | Umezawa et al. | 195/80 |
| 4,200,692 | 4/1980 | Puls et al. | |
| 4,301,251 | 11/1981 | Rumyantseva et al. | 435/267 |
| 4,390,559 | 6/1983 | Zilliken | |
| 5,141,746 | 8/1992 | Fleury et al. | |
| 5,320,949 | 6/1994 | Shen | 435/68.1 |
| 5,352,384 | 10/1994 | Shen | 252/398 |
| 5,506,211 | 4/1996 | Barnes et al. | 514/27 |
| 5,530,112 | 6/1996 | Greenshields et al. | 536/123.1 |
| 5,547,866 | 8/1996 | Durzan et al. | 435/123 |
| 5,554,519 | 9/1996 | Weber et al. | 435/125 |
| 5,637,561 | 6/1997 | Shen et al. | 514/2 |
| 5,700,669 | 12/1997 | Hanson et al. | 435/123 |
| 5,726,034 | 3/1998 | Bryan et al. | 435/68.1 |
| 5,763,389 | 6/1998 | Shen et al. | 514/2 |
| 5,789,581 | 8/1998 | Matsuura et al. | 536/128 |
| 5,792,503 | 8/1998 | Gugger et al. | 426/634 |

FOREIGN PATENT DOCUMENTS

| | | |
|---|---|---|
| 24813/97 | 12/1997 | Australia. |
| 0426998 A2 | 5/1991 | European Pat. Off.. |
| 61-246124A | 11/1986 | Japan. |
| 62-126186A | 6/1987 | Japan. |
| 01258669A | 10/1989 | Japan. |
| 02069165A | 3/1990 | Japan. |
| 03047049A | 2/1991 | Japan. |
| WO93/23069 | 11/1993 | WIPO. |
| WO94/23716 | 10/1994 | WIPO. |

OTHER PUBLICATIONS

Adlercreutz, H. et al., "Determination of Urinary Lignans and Phytoestrogen Metabolites, Potential Antiestrogens and Anticarcinogens, in Urine of Women on Various Habitual Diets," *J. Steroid Biochem*, vol. 25, No. 58, pp. 791–797 (1986).

Adlercreutz, Herman et al., "Dietary Phytoestrogens and Cancer In Vitro and In Vivo Studies," *J. Steroid Biochem Molec. Biol.*, vol. 41, No. 3–8 pp. 331–337 (1992).

Adlercreutz, Herman et al., "Dietary phyto-oestrogens and the menopause in Japan," *The Lancet*, pp. 1233 (1992).

Adlercreutz, H. et al., "Excretion of the Lignans Exterolactone and Enterodiol and of Equol in Omnivorous and Vegetarian Postmenopausal Women and in Women with Breast Cancer," *The Lancet*, pp. 1295–1299 (1982).

(List continued on next page.)

*Primary Examiner*—Cynthia L. Nessler
*Attorney, Agent, or Firm*—Finnegan, Henderson, Farabow, Garrett & Dunner, L.L.P.

[57] ABSTRACT

Processes for the production of isoflavones are described wherein plant material from plants of the genus leguminosae are contacted with water, an enzyme which cleaves isoflavone glycosides to the aglucone form and a $C_2$–$C_{10}$ organic solvent, so as to form a combination, incubating the combination for a time sufficient to allow isoflavones of the aglucone form to partition into the organic solvent component, and thereafter recovering isoflavones from the organic solvent component.

14 Claims, 1 Drawing Sheet

OTHER PUBLICATIONS

Adlercreutz, H. et al., "Lignans and Phytoesrogens", *Front. gastrointest. Res.,* vol. 14, pp. 165–176 (1988).

Adlercreutz, Herman et al., "Urinary Excretion of Lignans and Isoflavonoids Phytoestrogens in Japanese Men and Women Consuming a Traditional Japanese Diet," *Am. J. Clin. Nutr.,* vol. 54, pp. 1093–1100 (1991).

Adlercreutz, Herman, "Western Diet and Wester Diseases: Some Hormonal and Biochemical Mechanisms and Associations," *Scand. J. Clin. Lab. Invest,* Suppl., vol. 201 pp. 3–23 (1990).

Anderson M.D., James et al., "Meta–Analysis of the Effects of Soy Protein Intake on Serum Lipids," *New Eng. J. Med.,* vol. 333, No. 5, pp. 276–282 (1995).

Barnes, Stephen et al., "Soybeans Inhibit Mammary Tumors in Models of Breast Cancer," *Mutagens and Carcinogens in the Diet,* pp. 239–253 (1990).

Bailey, E.T. et al., "Isoflavone Concentrations in the Leaves of the Species of the Genus Trifolium, Section Calycomorphum," Aust. J. Agric. Res., vol. 22, pp. 731–736 (1971).

Bannwart, Christoph et al., "Identification of the Isoflavonic Phytoestrogen daidzein in Human Urine," *Clinica Chimica Acta,* vol. 136, pp. 165–172 (1984).

Barrow, N.J. et al., "Nutrient Potential and Capacity," *Aust. J. Agric. Res.,* vol. 17, pp. 849–861 (1966).

Barrow, N.J. et al., "Nutrient Potential and Capacity" (1966).

Beck, A.B., "The Oestrogenic Isoflavones of Subterranean Clover," *Aust. J. Agric. Res.* (1964).

Beckham, N., "Menopause," *The Family Guide to Natural Therapies,* Greenhouse Publications, pp. 41–42, 50 (1988).

Beckham, Nancy, "Herbal Help to Avoid Menopause Symptoms," *Australian Wellbeing,* No. 29, pp. 74–76 (1988).

Beckham, Nancy, "Phyto–Oestrogens and Compounds that Affect Oestrogen Metabolism—Part I," *Aust. J. Med. Herbalism,* vol. 7, No. 1, pp. 11–16 (1995).

Beckham, Nancy, "Phyto–Oestrogens and Compounds that Affect Oestrogen Metabolism—Part II," *Aust. J. Med. Herbalism,* vol. 7, No. 2, pp. 27–33 (1995).

Bennetts, H.W. et al., "A Specific Breeding Problem of Sheep on Subterranean Clover Pastures in Western Australia," *The Australian Veterinary Journal,* vol. 22, pp. 2–12 (1946).

Beuker Velasse—Advertising Brochure—with English language translation.

Bombardelli, Ezio, "Technologies for the Processing of Medicinal Plants," in *The Medicine Plant Industry,* Chapt. 7, pp. 85–98 (1991).

Bradbury, R.B. et al., "The Chemistry of Subterranean Clover. Part I. Isolation of Formononetin and Genistein," *J. Chem. Soc.,* pp. 3447–3449 (1951).

Bradbury, R.B. et al., "Estrogens and Related Substances in Plants," in *Vitamins and Hormones Advances in Research and Applications,* Harris, R.S. et al., eds., pp. 207–233 (1954).

Brandi, M.L., "Flavonoids: biochemical effects and therapeutic applications," *Bone and Mineral,* vol. 19 (Suppl.) S3–S14 (1992).

Braden, A.W.H. et al., "Comparison of Plasma Phyto–Oestrogen Levels in Sheep and Cattle After Feeding on Fresh Clover," *Aust. J. Agric. Res.,* vol. 22, pp. 663–670 (1971).

Braden, A.W.H. et al., "The Oestrogenic Activity and Metabolism of Certain Isoflavones in Sheep," *Aust. J. Agric. Res.,* vol. 18 pp. 335–348 (1967).

Circle, S. J. et al., "Processing Soy Flours, Protein Concentrates and Protein Isolates," *Soybeans: Chemistry and Technology,* vol. 1, pp. 294–338 (1972).

Coward, Lori et al., "Genistein, Daidzein, and Their $\beta$–Glycoside Conjugates: Antitumor Isoflavones in Soybean Foods from American and Asian Diets," *J. Agric. Food Chem.,* vol. 41, pp. 1961–1967 (1993).

Culbreth, David M.R., *A Manual of Materia Medica and Pharmacology,* pp. 19–22.

Davies, Lloyd H. et al., "Further Studies on Oestrogenic Activity in Strains of Subterranean Clober (*Trifolium Subterraneum* L.) In South–Western Australia," *Aust. J. Agric. Res.* (1965).

Davis, Harold et al., "Extraction," *Bentley's Text–Book of Pharmaceuticals,* 6th ed., XVIII, pp. 272–273 (1956).

Düker, Eva–Maria et al., "Effects of Extracts from *Clinicifuga Racemosa* on Gonadotropin Release in Menopausal Women and Ovariectomized Rats," *Planta Med.,* vol. 57, pp. 420–424 (1991).

Eldridge, Arthur C., "Determination of Isoflavones in Soybean Flours, Protein Concentrates, and Isolates," *J. Agric. Food. Chem.,* vol. 30, pp. 353–355 (1982).

Eldridge, A.C., "High–performance liquid chromatography separation of soybean iso–flavones and their glucosides," *J. Chrom.,* vol. 234 pp. 494–496 (1982).

Eldridge, Arthur C., "Soybean Isoflavones: Effect of Environment and Variety on Composition," *J. Agric. Food Chem.,* vol. 31 pp. 394–396 (1983).

Farmakalidis, Efi et al., "Isolation of 6"–O–Acetylgenistin and 6"–O–Acetyldaidzin from Toasted Defatted Soyflakes," *J. Agric. Food Chem.,* vol. 33, pp. 385–389 (1985).

Farmakalidis et al., Semi–Preparative High–Performance Liquid Chromatographic Isolation Soybean Isoflavones, *J. Chrom.,* vol. 295, pp. 510–514 (1984).

Farnsworth, Norman R., "Potential Value of Plants as Sources of New Antifertility Agents II," *J. Pharm. Sciences,* vol. 64, No. 5, pp. 717–754 (1975).

Francis., C.M. et al., "The Distribution of Oestrogenic Isoflavones in the Genus Trifolium," *Aust. J. Agric. Res.* (1966).

Francis, C.M. et al., "Varietal Variation in the Isoflavone Content of Subterranean Clover: Its Estimation by a Microtechnique," *Aust. J. Agric. Res.* (1965).

Gildersleeve, Rhonda R. et al., "Screening Rose Clover and Subterranean Clover Germplasm for Isoflavones," *Crop. Sci.,* vol. 31 pp. 1374–1376 (1991).

Gildersleeve, Rhonda R. et al., "Detection of Isoflavones in Seedling Subterranean Clover," *Crop Sci.,* vol. 31, pp. 889–892 (1991).

Gladstones, J.S., "Naturalized Subterranean Clover Strains in Western Australia: A Preliminary Agronomic Examination," *Aust. J. Agric. Res.,* vol. 8, pp. 713–731 (1967).

Herman, C. et al., "Soybean Phytoestrogen Intake and Cancer Risk," *American Institute of Nutrition,* pp. 7575–7705 (1995).

Holt, S., "Selected Bibliography of Scientific Studies on Genistein and Other Soya Isoflavones," *Soya for Health: The Definitive Medical Guide,* pp. 159–170 (1996).

Jenkins, David J.A. et al., "Leguminous seeds in the dietary management of hyperlipidemia[1–3]," *Am. J. Clin. Nut.,* vol. 38, pp. 567–573 (1983).

Jones, Amanda E. et al., "Development and Application of a High–Performance Liquid Chromatographic Method for the Analysis of Phytoestrogens," *J. Sci. Food Agric.,* vol. 46, pp. 357–364 (1989).

Kaldas, Rami S. et al., "Reproductive and General Metabolic Effects of Phytoestrogens in Mammals," *Reproductive Toxicology Review,* vol. 3, No. 2, pp. 81–89 (1989).

Kitada, Yoshimi et al., "Determination of Isoflavones in soy bean by high–performance liquid chromatography with amperometric detection," *J. Chrom.,* vol. 366, pp. 403–406 (1986).

Knuckles, Benny E. et al., "Coumestrol Content of Fractions Obtained During Wet Processing of Alfalfa," *J. Agric. Food Chem.,* vol. 24, No. 6, pp. 1177–1180, (1976).

Kudou, Shigemitsu et al., "A New Isoflavone Glycoside in Soybean Seeds (*Glycine max* Merrill), Glycitein 7–O–β–D–(6"–O–Acetyl)–Glucopyranoside," *Agric. Biol. Chem.,* vol. 55, No. 3, pp. 859–860 (1991).

Kudou, Shigemitsu et al., "Malonyl Isoflavone Glycosides in Soybean Seeds (*Glycine max* Merrill)," *Agric. Biol. Chem.,* vol. 55, No. 9, pp. 2227–2233 (1991).

Lindner, H.R., "Study of the Fate of Phyto–Oestrogens in the Sheep by Determination of Isoflavones and Coumestrol in the Plasma and Adipose Tissue," *Aust. J. Agric. Res.,* vol. 18, pp. 305–333 (1967).

Lock, Margaret, "Contested meanings of the menopause," *The Lancet,* vol. 337, pp. 1270–1272 (1991).

Martin, P.M. et al., "Phytoestrogen Interaction with Estrogen Receptors in Human Breast Cancer Cells," *Edocrinology,* vol. 193, No. 5, pp. 1860–1867 (1978).

Messina, Mark et al., "The Role of Soy Products in Reducing Risk of Cancer," *J. of National Cancer Institute,* vol. 83, No. 8, pp. 541–546 (1991).

Morris, P., "Identification and Accumulation of Isoflavonoids and Isoflavone Glucosides in Soybean Leaves and Hypocotyls in Resistance Responses to *Phytophthora Megasperma* f.sp. *Glycinea,*" *Physiological and Molecular Plant Pathology,* 39 pp. 221–244 (1991).

Murphy, P.A., Phytoestrogen Content of Processed Soybean Products, *Food Technology,* pp. 60–64 (1982).

Murphy, P.A., "Separation of Genistin, Daidzin and Their Aglucones, and Coumesterol by Gradient High Performance Liquid Chromatography," *J. Chrom,* vol. 211, pp. 166–169 (1991).

Naim, M. et al., "A New Isoflavone from Soya Beans," *Phytochemistry,* vol. 12, pp. 169–170 (1973).

Naim, M. et al., "Soybean Isoflavones, Characterization, Determination, and Antifungal Activity," *J. Agr. Food Chem.,* vol. 22, No. 5, pp. 806–810 (1974).

Nash, A.M. et al., "Fractionation and Characterization of Alcohol Extractables Associated with Soybean Proteins. Nonprotein Components," *J. Agr. Food Chem.,* vol. 15, No. 1, pp. 102–108 (1967).

Ohta, Naokazu et al., "Isoflavonoid Constituents of Soybeans and Isolation of a New Acetyl Daidzin," *Agric. Biol. Chem.,* 43, vol. No. 7, pp. 1415–1419 (1979).

Okano, Koji et al., "Isolation of Four Kinds of Isoflavon from Soya Bean," *Bron: Bull. Agr. Chem. Soc. Japan.* 15, vol. 15, p. 110 (1939).

Okubo, Kazuyoshi et al., "Components Responsible for the Undesirable Taste of Soybean Seeds," *Biosci. Biotech. Biochem.,* vol. 56, No. I, pp. 99–103 (1992).

Pope, G.S., "The Importance of Pasture Plant Oestrogens in the Reproduction and Lactation of Grazing Animals," *Dairy Science Abstracts,* vol. 16, No. 5, pp. 333–356 (1954).

Price, K.R. et al., "Naturally Occurring Oestrogens in Foods—A Review," *Food Additives and Contaminants,* vol. 2, No. 2 pp. 73–106 (1985).

Reinli, Kathrin et al., "Phytoestrogen Content of Foods—A Compendium of Literature Values," *Nutrition and Cancer,* vol. 26, No. 2, pp. 123–148 (1996).

Rose, David P., "Dietary Fiber, Phytoestrogens, and Breast Cancer," *Nutrition,* vol. 8, No. 1 (1992).

Rossiter, R.C., "Physiological and Ecological Studies on the Oestrogenic Isoflavones in Subterranean Clober (*T. Subterraneum* L.)," *Aust. J. Agric. Res.,* Chapter III (1966).

Rossiter, R.C., "Physiological and Ecological Studies on the Oestrogenic Isoflavones in Subterranean Clober (*T. Subterraneum* L.)," *Aust. J. Agric. Res.,* Chapter IV (1966).

Seo, A. et al., "Improved High–Performance Liquid Chromatographic Analysis of Phenolic Acids and Isoflavonoids from Soybean Protein Products," *J. Agric. Food Chem.,* vol. 32, No. 3, pp. 530–533 (1984).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chrom.,* vol. 386 pp. 315–323 (1987).

Setchell, K.D.R. et al., "Mammalian Lignans and Phyto–oestrogens Recent Studies on their Formation, Metabolism and Biological Role in Health and Disease," in Role of the Gut Flora In Toxicity and Cancer, pp. 315–339 (1988).

Setchell, KDR et al., "Nonsteroidal estrogens of dietary origin: possible roles in hormone–dependent disease," *Am. J. Clin. Nut.,* vol. 40 pp. 569–578 (1984).

Shimoyamada, Makoto et al., "Saponin Composition in Developing Soybean Seed (*Glycine max* (L.) Merrill, cv. Mikuriyaao)," *Agric. Biol. Chem.,* vol. 55, No. 5, pp. 1403–1405 (1991).

Shutt, Donald A., "The Effects of Plant Oestrogens on Animal Reproduction," *Endeavour,* vol. 35, pp. 110–113 (1976).

Shutt, D.A. et al., "Free and Conjugated Isoflavones in the Plasma of Sheep Followed Ingestion of Oestrogenic Clover," *Aust. J. Agric. Res.,* vol. 18 pp. 647–655 (1967).

Shutt, D.A., "Interaction of Genistein With Oestradiol in the Reproductive Tract of the Ovariectomized Mouse," *J. Endocrin.,* vol. 37, pp. 231–232 (1967).

Shutt, D.A. et al., "Quantitative Aspects of Phyto–Oestrogen Metabolism in Sheep Fed on Subterranean Clover (*Trifolium Subterraneum* Cultivar Clare) or Red Clover (*Trifolium Pratense*)," *Aust. J. Agric. Res.,* vol. 21, pp. 713–722 (1970).

Shutt, D.A. et al., "The Significance of Equol in Relation to the Oestrogenic Responses in Sheep Ingesting Clover With a High Formononetin Content," *Aust. J. Agric. Res.,* vol. 19, pp. 545–553 (1968).

Shutt, D.A. et al., "Steroid and Phyto–Oestrogen Binding to Sheep Uterine Receptors In Vitro," *J. Endocr.,* vol. 52, pp. 299–310 (1972).

Smith, G.R. et al., "Influence of Harvest Date, Cultivar, and Sample Storage Method on Concentration of Isoflavones in Subterranean Clover," *Crop Science,* vol. 26 (1986).

Trease, G.E. et al., "Pharmacognosy," $12^{th}$ Ed., pp. 242–260 (1983).

Verdeal, Kathey et al., "Naturally–Occurring Estrogens in Plant Foodstuffs—A Review," *J. Food Protect.,* vol. 42, No. 7, pp. 577–583 (1979).

Walter, E.D., "Genistin (an Isoflavone Glucoside) and its Aglucone, Genistein, from Soybeans," *J. Am. Chem. Soc.,* vol. 63, p. 3273 (1941).

Walz, E., "Isoflavon– und Saponin–Glucoside in Soja hispida", *Justus Leibigs Ann. Chem.,* vol. 489, pp. 118–155 (1931).

Wang, G. et al., "A Simplified HPLC Method for Determination of Phytoestrogens in Soybean and Its Processed Products," *J. Agr. Food Chem.,* vol. 38, No. 1, pp. 185–190 (1990).

White, Edmund et al., "Extracta," *Pharmacopedia,* 2d ed. (1909).

Wilcox, G. et al., "Oestrogenic effects of plant foods in post–menopausal women," *British Med. J.,* vol. 301, pp. 905–906 (1995).

Wong, E., "Detection and Estimation of Oestrogenic Constituents in Red Clover," *J. Sci. Food Agric.,* vol. 13, pp. 304–308 (1962).

Wong, E., "The Oestrogenic Activity of Red Clover Isoflavones and Some of Their Degradation Products," *J. Endocrin.,* vol. 24, pp. 341–348 (1962).

"Estrogenic Activity in Plants," Brisbane Seminar (Summary of Talk by Nancy Beckham) (1985).

The Merck Index, Eighth Edition (1968).

"Phenolic Constituents," *Soybeans: Chemistry and Technology,* vol. 1, pp. 186–189 (1972).

"Solvent Treatment of Beans and Fractions," *Soybeans: Chemistry and Technology,* p. 149 (1972).

"Uterine Weight Changes and $^3$H–Uridine Uptake in Rats Treated with Phytoestrogens," *Can. J. Anim. Sci.,* vol. 60 pp. 531–534 (1980).

PREPARATION OF ISOFLAVONES FROM LEGUMES

Isoflavones are plant chemicals which occur largely in members of the Leguminosae plant family. They are based on a simple diphenolic ring structure as described for example by Carlson et al (1980) Journal of Chromotography, 198, 193–197 (incorporated herein by reference).

Over 700 different isoflavones are described and these display a range of biological functions both within the plant and within animals including humans which eat the isoflavone-containing plants.

A small sub-group of isoflavones (daidzein, genistein, biochanin A, formononctin and glycitein) are distinguished by their ability to bind to estrogen receptors on animal (including human) cells. This is due to the close similarity of the steric structure of the diphenolic rings of isoflavones with the steroidal ring structure of estrogens such as estradiol, estrone and estriol. Although having substantially lower binding affinity to the receptor compared to steroidal estrogens, estrogenic isoflavones are weakly estrogenic. This group also exhibits a range of biological functions in animal cells which appear to be independent of the estrogen receptor and these include anti-oxidant, diuretic, anti-spasmolytic and anti cancer effects. These interesting functions with their potential therapeutic benefits has brought this particular group of isoflavones to the attention of medical researchers in resent years.

In the plant, the isoflavones can occur in a variety of forms—(i) in the basic aglucone form, (ii) as a glucone, being bound to a sugar moiety such as glucose via a $\beta$-glucosidic linkage, (iii) the glucone form+a malonyl moiety, and (iv) the glucone form+an acetyl moiety as described for example, by Carlson et al (1980) as referred to above.

The glycosidic form (either alone or in the malonyl or acetyl forms) is water-soluble and is the predominant form for the isoflavones in the plant to facilitate transport and storage. The glycosidic form also provides enhanced stability to degradative factors such as heat, oxidation and ultra-violet irradiation. At the intra-cellular site of biochemical function of the isoflavone, an intra-cellular $\beta$-glycosidase enzyme cleaves the sugar moiety, leaving the more biologically active, but substantially water-insoluble, aglucone form.

Isoflavones are fairly widely distributed within the plant kingdom although they are found predominantly in members of the Leguminosae family. The estrogenic isoflavones (genistein, biochanin, formononctin, daidzein, glycitein) follow this general rule in being largely restricted to the genus Leguminosae. Most legumes investigated have been found to contain at least detectable levels of one or more of these five estrogenic isoflavones but the richest sources are the legumes—soya, lentils, chick pea, fenugreek, clovers, alfalfa and various varieties of beans. The richest sources of these compounds are the clovers (*Trifolium pratense, Trifolium sub-terranean*) and soya (either whole soya or defatted soya or any materials ensuing as products of soya processing including soya grits, soya hypocotyls and soy molasses). The levels of these compounds in clovers and soya varies according to the variety or cultivar and on seasonal, environmental and plant age factors. Levels in clovers vary between about 0.5 and 3.5% (on dry weight basis) and in soybeans between about 0.05 and 0.3% (dry weight).

Isoflavones may be used as therapeutics for pre-menstrual syndrome and menopausal syndrome (U.S. Pat. Nos. 5,569,459, 5,516,528, 5,498,631) and osteoporosis (U.S. Pat. No. 5,424,331) and as food additives (U.S. Pat. Nos. 4,366,082, 4,390,559). Given these important uses, it is advantageous to isolate or to concentrate isoflavones from plants.

Various techniques have been proposed to achieve this, but essentially there are two distinct methods. The first method involves the conversion of the water-soluble glucone form to the water-insoluble aglucone form to facilitate the subsequent extraction of the aglucones in a suitable organic solvent such as alcohol. This conversion step is described as being achieved in one of two ways: either (a) through hydrolysis by exposure to vigorous heater (typically 80–100° C.) at low pH (Wang K, Kuan S S, Francis O J, Ware K M, Carman A S. "A simplified HPLC method for the determination of phytoestrogens in soybean and its processed products." *J. Agric. Food Chem.* 38:185–190, 1990); or (b) by exposure to an enzyme (glucose hydrolase, $\beta$-glycosidase or $\beta$-glucoronidase) which specifically cleaves the $\beta$-glycosidic linkage with the sugar moiety. The enzyme either is added to the reaction or the naturally occurring $\beta$-glucosidase within the plant can be utilised. In respect to the latter, a method is described (JP 89-345164/47) whereby the natural enzyme activity within soybeans is utilised by heating soyflour to 45–55° C. for several hours, although the amount of naturally-occurring enzyme activity in commercially available soyflour samples is highly variable and even when at its maximum is insufficient to obtain hydrolysis of more than about 50–60% of the glucones present.

The various hydrolysis reaction procedure (either enzymatic or heating/low pH) is described as being applied to an admixutre of ground plant material in water. At the conclusion of the hydrolysis process, the aqueous phase is separated from the undissolved plant material to facilitate the next step. Once the conversion of the glucone to the aglucone form is achieved, the aqueous mixture then is contacted with an organic (and water immiscible) solvent. The aglucones due to their substantial water insolubility are extracted into the organic solvent phase and subsequent recovered.

The second method involves initial water extraction of the isoflavones in their aglucone form so that they either are retained in this form or can be converted subsequently to their aglucone form. The techniques described for this approach involve adding the ground plant material to water and over a period of time (several hours to several days) the naturally-occurring glycosidic forms of the isoflavones dissolve in the aqueous phase. After separating the undissolved plant material from the aqueous phase, the isoflavones in the aqueous phase are converted to the aglucone form by any of the methods outlines above and subsequently recovered. A variant of this process involves selective removal of the aglucone forms from the aqueous mixture by absorption onto an appropriate ion-exchange resin. The isoflavones subsequently are eluted from that resin using a water:organic solvent mixture, concentrated by rotary evaporation, and then hydrolysed to the aglucone form by enzymatic digestion or heat/acid treatment (JP 95-272884/36).

Disadvantages of the above techniques include (a) a multiplicity of steps, (b) the use of vigorous treatments such as heating and/or strong acid and/or strong alkali, (c) the comparatively low yields of isoflavones, (d) the very high cost of hydrolysing enzymes, and (e) the high capital costs and a high running costs associated with large-scale extraction of isoflavones in commercial quantities. All of the current known isoflavone extraction procedures are affected by one or more of these disadvantages and serve to greatly reduce the commercial viability of the process. If the purported community health benefits of the estrogenic isoflavones are to be realised then they must become economically accessible to the general community. For this to happen, an improved and more cost-effective method of extraction must be found.

SUMMARY OF THE INVENTION

In the broadest aspect of this invention there is provided processed for the production of isoflavones from plants of the genus Leguminosae which comprises contacting plant material with water, and enzyme which cleaves isoflavone glycosides to the aglucone form, and a $C_2$–$C_{10}$ organic solvent, to form a combination, and incubating the combination for a time sufficient to allow isoflavones of the aglucone form to partition into the organic solvent component, and thereafter recovering isoflavones from the organic solvent component.

The combination of the aforementioned components may comprise an aqueous phase containing enzyme and plant material and an organic phase into which the isoflavones partition. The combination may alternatively comprise an emulsion formed by vigorous mixing of the organic solvent and water.

Preferably the enzyme used to cleave isoflavone glycosides to the aglucone form comprises a β-glucanase. More preferably the enzyme is a mix (or combination) of β-glucanase and β-xylanase.

The described process preferably occurs without the need for applied heat or the adjustment of pH and takes place within a single reaction vessel and with a minimum of steps.

DETAILED DESCRIPTION OF THE INVENTION

Figure 1:
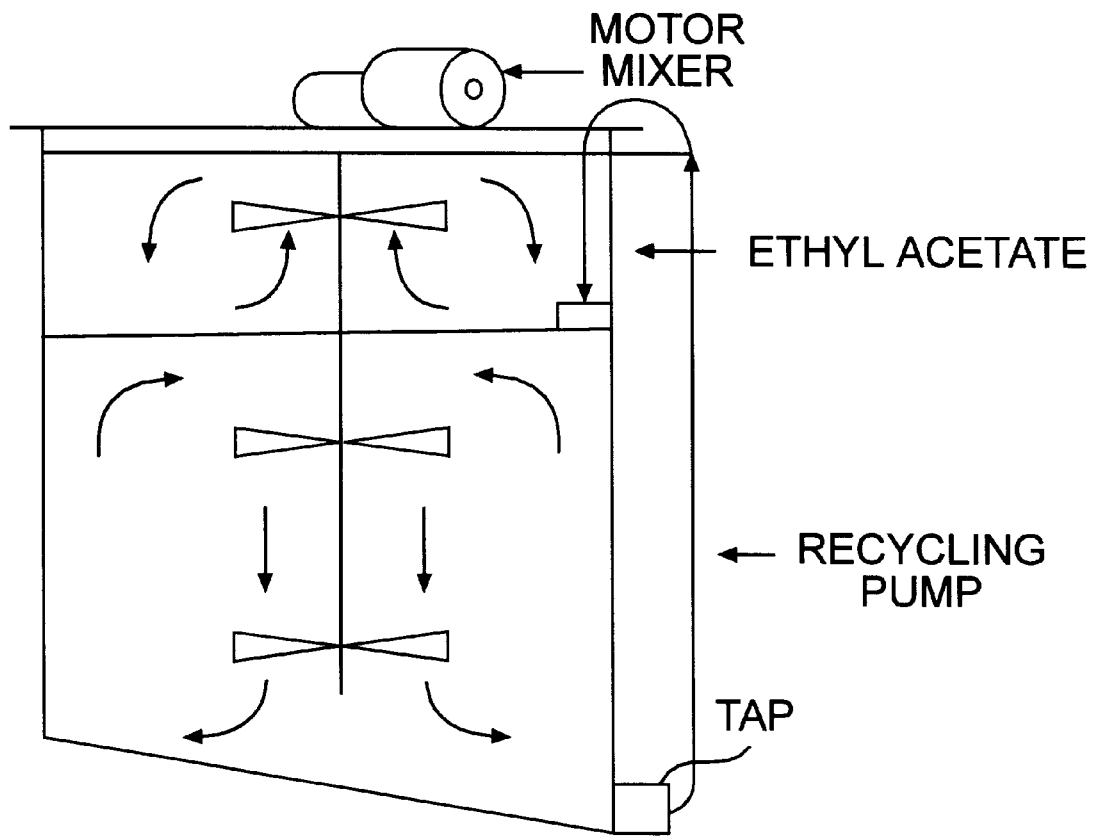
FIG. 1 is a diagram of a mixer which may be used in accordance with an embodiment of the invention.

The present invention provides in its broadest aspect a process for the production of isoflavones from plants of the genus Leguminosae which comprises contacting plant material with water, an enzyme which cleaves isoflavone glycosides to the aglucone form, and a $C_2$–C10 organic solvent, to form a combination and incubating the combination for a time sufficient to allow isoflavones of the aglucone form to partition into the organic solvent component, and thereafter recovering isoflavones from the organic solvent component.

The combination which results from combining together the plant material, water, the enzyme which cleaves isoflavone glycosides to the aglucone form, and a $C_2$–$C_{10}$ organic solvent may be in the form of a separated phase mixture comprising an aqueous phase containing the enzyme and plant material and an organic phase into which isoflavones partition on incubation following cleavage by the enzyme. The combination may comprise an emulsion formed by vigorous mixing of the organic solvent and water. Where the combination comprises an emulsion it is preferred to remove particulate material from the emulsion, after a period of time sufficient to enable the aglucone form of the isoflavone to partition into the organic solvent, using a standard separation process such as filtration or centrifugation. Phase separation then occurs, this subsequently allowing recovery is isoflavones from the organic solvent component.

The enzyme used to cleave the isoflavone glycoside to the aglucone form (hereinafter referred to as isoflavone) is required specifically to cleave the β-glycosidic linkage which is described as the dominant linkage between the isoflavone and its carbohydrate (normally glucose) moiety. A person skilled in the field of carbohydrate chemistry would deduce that the most appropriate enzyme to achieve this would be a β-glucosidase and possibly a β-glucanase. As Table 1 shows, in an experiment to compare the relative potencies of different carbohydrate enzymes in their ability to cleave the glycosidic linkage of soy isoflavones, it was found that β-glucosidase was highly effective; β-glucoronidase was found unexpectedly also to be highly effective; β-glucanase unexpectedly was found to have relatively low potency and required a considerably longer reaction time.

TABLE 1

Comparative actions of different carbohydrate-acting enzymes in converting soya isoflavones in their glycosidic forms (daidzin, genistin) to the aglucone forms (daidzein, genistein).

| Enzyme type* | Relative activity (% conversion) |
|---|---|
| β-glucosidase | 90 |
| β-glucuronidase | 98 |
| β-glucanase | 40 |
| 1,4-bD-glucan hydrolase | 0 |
| 1,4-a-D-glucan hydrolase | 0 |
| β-xylanase:b-glucanase (10:1) | 85 |
| β-xylanase:b-glucanase (1:1) | 87 |

*All enzymes added at the same concentration to a standard amount of isoflavone.

A β-glucanase/β-xylanase enzyme mix was found by the inventors to be relatively effective in cleaving the isoflavone glycoside to the aglucone form. This was entirely unexpected given that there was no reason to expect that a β-xylanase would have any effect on the described form of glycosidic linkage on the isoflavone glucone form. Advantageously, this fungal-derived enzyme mix is available in large commercial quantities at an advantageous cost. Although only slightly less efficient than the more specific b-glucosidase and β-glucoronidase enzymes, the latter enzymes are not available in bulk, commercial quantities or at cost-effective prices. Moreover, the low cost of the commercial β-glucanase/β-xylanase enzyme mix allowed the dosage per unit of isoflavone to be increased which more than compensates for the slightly lowered efficiency. Importantly, in the process of forming the combination, the organic solvent does not cause significant inactivation of the enzyme used.

The plant material is derived from plants of the genus Leguminosae and may be obtained from plants such as soy, clover (including subterranean clover, red clover, and other isoflavone-containing clovers), chickpeas, lentils, beans (such as broad, haricot, kidney, lima and navy beams) which generally contain higher levels of isoflavones than other plants of the genus Leguminosae. It is preferred that the plant material be derived from soy or clover although this is not to say that other isoflavone containing plants of the genus Leguminosae may not be used in the process of this invention.

The plant material is preferably in fine particulate form, such as a flour produced by grinding or otherwise processing plant material such as clover, soy beans, other beans, chickpeas and lentils. The preferred plant material is soya (*Glycine max*). Without limiting the present invention, it is preferable to remove as much as possible of parts of the plant that do not contain isoflavones to any great extent in order to reduce the bulk of material to be exposed to the extraction process. For example, about 90% of the isoflavones contained in harvested clovers occurs in the leaves and about 10% of the stalks and petioles so it is advantageous to separate the leaves form the stalks which can be achieved by first exposing the dried plant to a threshing action followed by differential sieving to separate the smaller leaves from the larger stalks. In another example, soybeans may be dehulled and/or defatted and dehulled. Defatted soyflour is readily available in commercial quantities. In another example, soy hypocotyl which often breaks away from the soy cotyledons during regular dehulling processes and is readily connected by standard methods such as sieving, contains typically higher isoflavone levels (between about 0.5 and 1.5%) compared to the whole soybean (between about 0.05 and 0.3%).

The solvent utilised in the process of this invention comprises from 2 to 10 carbons ($C_2$–$C_{10}$) and importantly is water-immiscible. Any solvent or mixture of solvents conventionally used in the process of purifying isoflavone compounds from plant material may be utilised. Examples of solvents which may be used include $C_2$–$C_{10}$ alcohols (such as butanol, hexanol and pentanol); $C_1$–$C_{10}$ alkoxy solvents (such as ethyl methyl ketone, methyl phenyl ketone, hexane-2,4-dione and the like); $C_2$–$C_{10}$ esterified acids (such as ethyl acetate, ethyl methyl malonate, dimethyl phosphonate); $C_4$–$C_8$ aldehydes (including butanone, pentanone, hexanedial, cyclohexane carbaldehyde and butane-1,2,4-tricarbaldehyde); $C_2$–$C_{10}$ ethers, or phenol and its derivatives (such as benzene 1,2,4-thiol). Organic solvents may be mixed. Ethyl acetate is a preferred organic solvent. The organic solvent is selected to have a volatility to enable the organic solvent to be removed (for example by distillation, rotary evaporation and the like) so that isoflavone compounds in the organic solvent can be subsequently recovered.

The water used in the process may be from any conventional water source, distilled water, deionized and distilled water or the like. The water may contain preservatives to retard microbial growth and/or other additives as are well known in the art. The respective proportions of water and organic solvent are not limiting on this invention. Generally equal proportions of water and organic solvent are used, although the ratio of water to organic solvent may vary, for example from 1:10 to 10:1.

Where the combination resulting from the mixture of the water and organic solvent comprises an organic phase and an aqueous phase the respective phases may be gently mixed or agitated. This can easily be achieved by a vertically disposed stirrer which allows mixing of the respective phases without intermixing of the phases as such.

The process of the invention does not require elevated temperatures and may be conducted under ambient temperature conditions, for example from 5° C. to 35° C. Ambient temperature conditions can therefore suffice under most circumstances without the need for sophisticated temperature control as is required in prior art processes where elevated extraction temperatures are necessary.

It is to be noted that the extraction process of the present invention is a one pot, single stage reaction which confers substantial benefits such as cost savings in capital equipment expenditure and in time. The performance of enzymatic digestion and solvent extraction in one step is very efficient and gives high yield of isoflavone products, which is generally in contrast to prior art procedures.

Isoflavone compounds are recovered from the organic solvent component generally by vaporisation of the organic phase such as by rotary evaporation, distillation or the like.

A small amount of oil containing the aglucone isoflavones is found to remain following removal of the organic phase. This isoflavone-enriches oil may be regarded as the desired end product and used as such, although it is preferable to continue the extraction process to further concentrate the isoflavones. The oil then is removed by the addition of a suitable organic solvent such as hexane, heptane and octane which are highly soluble for oils but very low solubility for isoflavones; hexane preferably is used because of its relatively low cost. The solvent (such as hexane) is added at a ratio to the oil of between about 1:1 and 50:1, preferably 10:1. It is found that the oil readily partitions in the organic solvent phase and that this is associated with the isoflavones falling out of solution and settling to the bottom of the vessel. The hexane:oil phase then is removed leaving the isoflavone-containing residue. This may be recovered and dried, such as in an oven at a temperature between about 50° C. to 120° C., to produce a fine powder. Preferably, however, the hexane extraction step is repeated a further 1–3 times to effect complete removal of oil.

At this stage the extraction material is of high isoflavone content, such as from 36 to 70% isoflavones, and generally is comparable to the ratio of isoflavones of the starting material. As a consequence the yields are typically very high. The material may be used for therapeutic purposes at that point, or can be subject to further processing as is known in the art to further purify the isoflavone. Further purification may comprise HPLC fractionation, ion exchange chromatography or other techniques as are well known in the art.

Where soy is the starting material, the isoflavones extracted are daidzein, genistein, and glycitein; the remaining material is composed of a range of compounds including phytosterols and other water-insoluble compounds. Where clover is the starting material, the isoflavones extracted are daidzein, genistein, formononetin, biochanin and pratensein; various flavonoids including chlorophyll as well as phytosterols make up the bulk of the remainder of the isolate.

The isoflavones may be formed into pharmaceutical compositions or health compositions, drinks, foods and the like, in combination with appropriate excipients, carries and the like as are well known in the art, for example as described in *Handbook of Pharmaceutical Excipients,* Second Edition, American Pharmaceutical Association, 1994 (incorporated herein by reference). Pharmaceutical compositions or health compositions may comprise tablets, capsules, powders for reconstitution, syrups and the like. Foods containing isoflavones may comprise food bars, biscuits, snack foods and other standard food forms well known in the art. Drinks may contain flavouring, buffers and the like.

It would appear that the prior art has not contemplated the use of a one pot process for converting isoflavones from the glucone to the aglucone form at the same time as recovery of the agluconic isoflavones in an organic solvent for a number of reasons. It may have been believed necessary to remove residual leguminous plant material from the process after cleavage of the glycoside form. It may also have been regarded that organic solvent would inactivate the enzymes used to effect formation of the aglucone form. As a consequence, conversion of the water soluble glucone form to the water insoluble aglucone form has been carried out in one step, followed by a subsequent step of extraction of the aglucones in a suitable organic solvent.

This invention will now be described with reference to the following non-limiting drawings and examples.

EXAMPLE 1

7,000 kg of defatted soyflour is placed in a 10,000 L vessel as depicted in FIG. 1 containing 5,000 L of deionised water and 10 kg of β-glucanase/b-xylanase (Bio-Feed Beta CT; Novo Nordisk, Denmark). 1000 L of ethyl acetate is then layered on top of the aqueous suspension to give a two phase combination. Both aqueous and solvent phases are gently mixed by continuous stirring using a vertical propeller mixer (FIG. 1). It is found that at the point of contact between the aqueous and organic solvent phases, the aglucone isoflavones readily move from the aqueous to the organic solvent phase. The constant agitation of the aqueous phase is designed to ensure maximum exposure of the hydrolysed isoflavones to the ethyl acetate; the constant agitation of the ethyl acetate helps to ensure a high isoflavone concentration gradient between the two phases, thereby maximising the rate of dissolution of the water-insoluble aglucone form into the ethyl acetate. An optional further contact between the two phases may be provided by circulating the lower aqueous suspension through the ethyl acetate phase.

After about 4 to about 48 hours, but preferably around 18 hours, the agitation and recirculation processes are stopped and the two phases allowed to separate maximally. The ethyl acetate is removed and evaporated using a still. About 20 L of oil remains unevaporated. 200 L of hexane is added to the oil and mixed vigorously by stirring for about 5 minutes. This is allowed to stand overnight (about 18 hours) without stirring and it is found that particulate material containing the aglucone isoflavones settles to the bottom of the reaction vessel. The hexane:oil phase is decanted leaving a sludge. A further 5 l of hexane is added to the sludge to effect removal of residual oil. This mixture is allowed to stand for 1 hour by which time the particulate material has settled out once again. The hexane:oil phase is decanted leaving a semi solid sludge which is collected and dried in an oven at a temperature of about 85° C. By HPLC analysis this material is found to contain between about 36–70% (typically about 60%) isoflavones. Importantly, the ratio of the isoflavones in the extract is comparable to that of the starting material and the isoflavone yields typically are very high (Table 2). This material can be used for the purpose as is, or can be subjected to further processing in order to further purify the isoflavones.

TABLE 2

Recovery of isoflavones from whole soyflour using the extraction method described in Example 1.

| Isoflavone | % recovery of starting material |
| --- | --- |
| daidzein | 80.3 |
| genistein | 76.3 |
| glycitein | 75.0 |

EXAMPLE 2

The starting material is 200 kg of soy grits containing a mixture of soy hypocotyls and pieces of soy cotyledons and representing a more enriched source of isoflavones (about 10.% compared to about 0.2% on whole soyaflour). 200 kg of soy grits is placed in a 3000 L vessel containing 1000 L of deionised water and 2.5 kg of glucan hydrolase (Bio-Feed Beta CT; Novo Nordisk, Denmark). 1000 L of ethyl acetate is then added and the aqueous and solvent phases then mixed together vigorously using a pump with a capacity of about 200 L per minute to ensure effective contact between the two phases, that is, form an emulsion. The mixing continues at room temperature for a period of between 1–20 hours, but preferably 4 hours. The particulate material in this combination is then separated from the liquid phase by a standard process such as filtration or centrifugation. The removal of the particulate material destroys the emulsion, and on allowing the resulting liquid phase to stand for about 30 minutes there is effected separation between the aqueous and the ethyl acetate phases. The ethyl acetate which contains the isoflavones then is removed and exposed to distillation. The residual oil remaining after distillation of the ethyl acetate then is treated according to the steps outlined in Example 1 above to isolate the isoflavone enriched material.

EXAMPLE 3

The dried end product of Examples 1 and 2 above (Sample 1) can be used as starting material to concentrate genistein or daidzein with/without glycitein. 3 kg of this material is mixed with 1000 L of an organic solvent such as acetone, chloroform or octanone, but preferably acetone for reasons of safety and cost. Each of these 3 solvents has been shown by the inventors to have high affinity for genistein but not daidzein or glycitein. The mixture is stirred continuously at room temperature for between 1–24 hours but preferably 2 hours during which time a large amount (approximately 75%) of the genistein transfers into the solvent phase. The mixture is allowed to settle for about 2 hours, the solvent separated from the residue (Sample 2) and transferred to a still for evaporation. The residue left after evaporation of the solvent (Sample 3) contains genistein at a purity of between 90–94% (mean 92%), with the residual material being daidzein and glycitein. Sample 2 material preferably is extracted with acetone a further 1–5 times (preferably 4 times), by which time no more than about 1–5% of the original genistein in Sample 1 remains in the material. The composition of Sample 2 typically is by weight daidzein 55%, glycitein 15% and other material 30% and in Sample 3 typically is by weight genistein 91%, daidzein 4%, glycitein 2% and other 3%. The genistein in Sample 3 can be purified further by dissolving the dried material in 50 L of ethanol at about 80° C. and then reducing the volume of ethanol by a standard method such as rotary evaporation. As the volume of ethanol reduces to about 15 L (i.e. to about 30% of the starting volume), genistein selectively begins to crystallise. The ethanol then is allowed to cool overnight at ambient temperature and atmospheric pressure. About 85–90% of the genistein in the starting Sample 3 will have crystallised overnight, but only about 5–12% of the daidzein and glycitein. The ethanol is decanted leaving a crystalline reside which is air-dried. This material contains genistein to about 95–99% (typically 98.5%) purity, which may be regarded as being in substantially pure form.

EXAMPLE 4

Pharmaceutical compositions can be prepared from the products extracted according to the examples above.

1. The following composition is prepared in the form of a tablet:
   Using soyflour extract prepared according to Example 1 and containing (genistein 35% and daidzein 28% by weight)
   60 mg of extract
   340 mg of a standard tablet inert carrier
   This composition is tableted to provide a 400 mg tablet containing 20 mg of genistein and 17 mg daidzein.
2. The following composition is prepared in the form of a capsule:
   Using soy hypocotyl extract prepared according to Example 2 and containing (genistein 18%, daidzein 35% and glycitein 18% by weight)

60 mg of extract 190 mg of a standard pharmaceutical inert carrier

All contained in a non-toxic gelatic capsule and providing 200 mg containing approximately 11 mg of genistein, 21 mg of daidzein and 1 mg of glycitein.

3. The following composition is prepared in the form of a tablet:

Using Sample 2 extract prepared according to Example 3 and containing (daidzein 52%, glycitein 15% and genistein 3% by weight)

60 mg of extract 340 mg of a standard tablet inert carrier

This composition is tableted to provide a 400 mg tablet containing 31 mg of daidzein, 9 mg of glycitein and 2 mg of genistein.

4. The following composition is prepared in the form of a tablet:

Using Sample 3 extract prepared according to Example 3 and containing (genistein 99.5% by weight)

50 mg of extract 150 mg of a standard tablet inert carrier

This composition is tableted to provide a 200 mg tablet containing 50 mg of genistein.

The carriers referred to above include cellulose (microcrystalline), calcium hydrogen phosphate, soy polysaccharide, magentisum stearate and silica-colloidal (anhydrous).

What is claimed is:

1. A process for the production of isoflavones from plants of the genus Leguminosae which comprises a contacting plant material with water, a supplemental enzyme which cleaves isoflavone glycosides to the aglucone form, and a $C_2$–$C_{10}$ organic solvent to form a combination, incubating the combination for a time sufficient to allow isoflavones of the aglucone form to partition into the organic solvent component, and thereafter recovering isoflavones from the organic solvent component.

2. A process according to claim 1 wherein the combination comprises an aqueous phase containing the enzyme and plant material and an organic phase into which the isoflavones partition.

3. A process according to claim 1 wherein the combination comprises an emulsion formed by vigorous mixing of the organic solvent and water.

4. A process according to claim 1 wherein the enzyme is a β-glucanase and β-xylanase mixture.

5. A process according to claim 1 wherein the plant material is mixed with the water and the enzyme whereafter the organic solvent is added so as to form an organic phase and an aqueous phase, or an emulsion formed by vigorous mixing of the organic solvent and water.

6. A process according to claim 1 wherein the plant material is mixed with water, whereafter the enzyme is added with the organic solvent.

7. A process according to claim 1 wherein the plant material is from soy or clover.

8. A process according to claim 2 wherein both the aqueous phase and the organic phase are gently mixed.

9. A process according to claim 1 which is carried out at from 10° C. to 30° C.

10. A process according to claim 1 wherein the plant material is in particulate form.

11. A process according to claim 10 wherein the plant material is soy flour.

12. A process according to claim 10 wherein the plant material is a variable mixture of soy hypocotyls and soy cotyledons.

13. A process according to claim 1 wherein the isoflavones recovered from the organic solvent component are reacted with a solvent which preferentially dissolves genistein whereafter the genistein is recovered in substantially pure form from the solvent phase.

14. A process according to claim 1 wherein daidzein is recovered from the isoflavones following reaction with the solvent.

* * * * *